United States Patent
Walter

(10) Patent No.: US 8,347,769 B2
(45) Date of Patent: Jan. 8, 2013

(54) DEVICE AND METHOD FOR CONTROLLING A BRAKE OF A MICROTOME

(75) Inventor: Roland Walter, Neulussheim (DE)

(73) Assignee: Leica Biosystems Nussloch GmbH, Nussloch (DE)

( * ) Notice: Subject to any disclaimer, the term of this patent is extended or adjusted under 35 U.S.C. 154(b) by 400 days.

(21) Appl. No.: 12/602,159

(22) PCT Filed: Jun. 5, 2008

(86) PCT No.: PCT/EP2008/056969
§ 371 (c)(1),
(2), (4) Date: Nov. 30, 2009

(87) PCT Pub. No.: WO2008/148835
PCT Pub. Date: Dec. 11, 2008

(65) Prior Publication Data
US 2010/0175525 A1    Jul. 15, 2010

(30) Foreign Application Priority Data

Jun. 6, 2007 (DE) .......................... 10 2007 026 843

(51) Int. Cl.
*B26D 1/00* (2006.01)
*B23Q 15/00* (2006.01)
(52) U.S. Cl. ................................ 83/13; 83/72; 83/915.5
(58) Field of Classification Search ................... 83/76.9, 83/68, 915.5, 13, 72
See application file for complete search history.

(56) References Cited

U.S. PATENT DOCUMENTS
4,181,206 A * 1/1980 Seilenbinder ................. 477/174
(Continued)

FOREIGN PATENT DOCUMENTS
DE 199 11 163 7/2000
DE 92 19 220 U1 9/2000

OTHER PUBLICATIONS
The International Bureau of WIPO, International Preliminary Report on Patentability (English Translation), International Application No. PCT/EP2008/056969, Jan. 12, 2010, Switzerland.

*Primary Examiner* — Sean Michalski
(74) *Attorney, Agent, or Firm* — Hodgson Russ LLP

(57) ABSTRACT

The present invention relates to a device for controlling a brake of a microtome. The microtome (1) has an actuating element (2), a movement mechanism (8) and a brake. With the aid of the movement mechanism (8), an object to be cut can be moved relative to a knife blade. The actuating element (2) can be manually actuated by an operator and, as a result thereof, the relative motion between the object and the knife blade can be performed with the movement mechanism (8). The relative motion can be locked with the aid of the brake. So that the relative motion between the object and the knife blade can be used in a mechanically designed movement mechanism (8) and/or the relative motion can be locked without an additional hand movement of the operator, the inventive device is characterized by at least one sensor unit (5, 13). The sensor unit (5, 13) is provided on the actuating element (2) or adjacent to the actuating element (2). With the aid of the sensor unit (5, 13) a contact by the operator can be determined. The device is further characterized by a control of the brake depending on a contact by the operator determined or not determined by the at least one sensor unit (5, 13).

15 Claims, 2 Drawing Sheets

U.S. PATENT DOCUMENTS

| | | | |
|---|---|---|---|
| 4,839,533 A * | 6/1989 | Aga | 307/140 |
| 5,043,907 A * | 8/1991 | Richards | 700/167 |
| 5,065,657 A | 11/1991 | Pfeifer | |
| 5,181,443 A * | 1/1993 | Sitte et al. | 83/72 |
| 5,197,361 A * | 3/1993 | Carrier et al. | 82/1.2 |
| 5,461,953 A * | 10/1995 | McCormick | 83/36 |
| 5,630,487 A * | 5/1997 | Hamman et al. | 188/353 |
| 6,598,507 B1 | 7/2003 | Guenther et al. | |
| 2006/0272467 A1 * | 12/2006 | Hendrick et al. | 83/730 |
| 2008/0091309 A1 * | 4/2008 | Walker | 701/1 |

\* cited by examiner

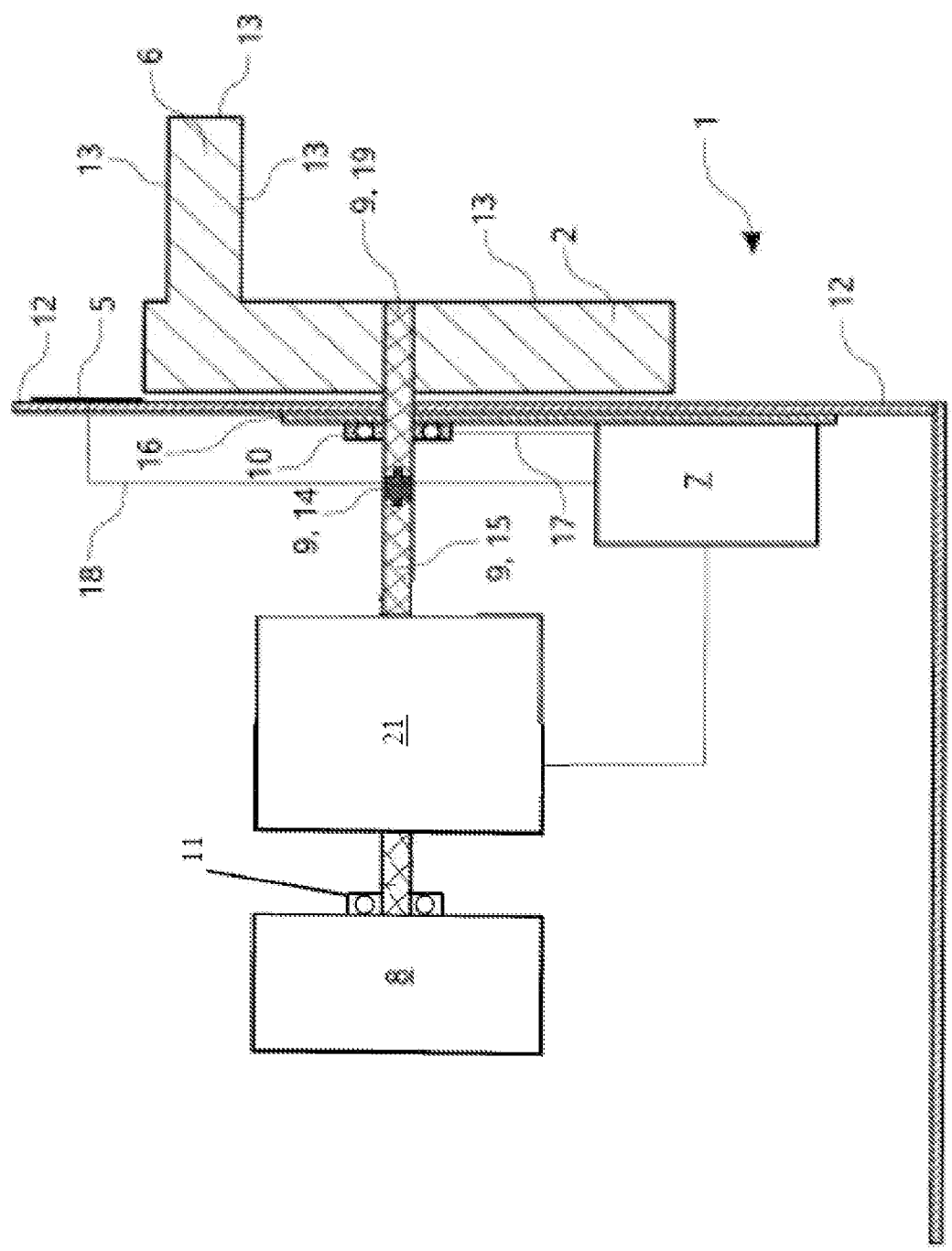

DEVICE AND METHOD FOR CONTROLLING A BRAKE OF A MICROTOME

The present invention relates to a device for controlling a brake or locking device of a microtome. The microtome has an actuating element, a movement mechanism and a brake. The actuating element is in particular designed in the form of a handwheel. By means of the movement mechanism an object to be cut can be moved relative to a knife blade. The actuating element can be manually actuated by an operator and, as a result thereof, the relative motion between the object and the knife blade can be performed or controlled by means of the movement mechanism. By means of the (activated) brake the relative motion can be locked. Further, the present invention relates to a method for controlling a brake of a microtome.

Microtomes have been known from the prior art for a long time. By means of a microtome, fine tissue sections can be produced from a tissue sample embedded in paraffin, which sections can then be placed on a slide for microscopic examination. There are microtomes in which the object—except for a feed motion—is clamped in a holder on the housing of the microtome so as to be immovable, and in which the knife blade is moved relative to the object or, respectively, to the microtome housing. This is particularly the case for slide microtomes and disc microtomes.

In the case of rotary microtomes—except for a feed motion—the knife blade is arranged fixed to the housing and the clamped object is arranged movably relative to the knife blade. The movement mechanism of a rotary microtome can be driven mechanically or can be motor-driven, for example, by means of an electric motor. When working with the microtome, it is, inter alia, necessary to adjust the object or the tissue sample at the clamping device for the embedded tissue sample—the so-called object head—or to clamp another tissue sample. If the object head is arranged freely movably, it may happen that the operator cuts himself/herself. This is particularly disadvantageous as the tissue samples usually contain contaminated or bacterially contaminated biological material, and thus there is an acute risk of infection for the operator of the microtome. This is why the movable parts of the object head can be arrested or locked.

Thus, for example, from DE 199 11 163 C1 a movement mechanism for moving the object head is known, which mechanism is driven by an electric motor. Here, an automatic blocking or locking of the object head is caused by a direct blocking of the drive or, respectively, the electric motor. In case a microtome does not have an electric drive, a locking lever mechanically actuated by an operator could be provided on or near the actuating element or handwheel, by means of which the handwheel and thus the movement mechanism and eventually also the object head can be locked. Such a locking lever is shown in FIG. 1 indicated by the reference sign 20 and is—per se—known from the prior art. This, however, requires an additional hand movement or work step so that this locking possibility is not used by all operators.

Therefore, the object of the present invention is to specify and develop a device for controlling a brake of a microtome, which device can be used in a mechanically designed movement mechanism. It is also desirable to control the brake for locking the relative motion between the object and the knife blade without an additional hand movement of the operator.

The inventive device of the type mentioned at the beginning solves the above object by the features described herein. Accordingly, such a device is characterized by at least one sensor unit. The sensor unit is provided on the actuating element or adjacent to the actuating element. Thus, the sensor unit could, for example, be provided on the housing of the microtome. With the sensor unit, a contact by the operator can be determined. The device is further characterized in that the brake is controlled depending on a contact by the operator that is determined or not determined by the at least one sensor unit. Particularly preferably, the brake is controlled automatically.

According to the invention, it has first of all been found that the brake is not to be activated or, respectively, the relative motion between the object and the knife blade is not to be locked, when the operator of the microtome actuates the actuating element. As in this case, the operator controls via the actuating element the movement mechanism for the relative motion between the object and the knife blade. Insofar it is quite unlikely that he/she simultaneously works on the object to be cut or on the object head. Therefore, in this case there is no acute risk of injury for the operator, which would require a locking of the object. Consequently, according to the invention the actuation or the contact of the actuating element is detected or determined by means of a sensor unit and, depending on whether a contact of the actuating element can be determined with the sensor unit or whether a contact cannot be determined, the brake is controlled. By this way of proceeding it is advantageously not necessary to provide a locking lever which, with an additional action of the operator, has to be actuated each time during locking and unlocking of the brake. In all, the operation of the microtome is thus facilitated and the ease and convenience in operation are increased. The safety during the operation of the microtome can also be considerably increased as a result thereof, since—provided that there is an appropriately automatically designed control of the brake—the operator does not have to perform an additional hand movement in order to lock or release the brake and, accordingly, a possible inadvertence of the operator does no longer pose a safety risk or a risk of injury.

According to a particularly preferred embodiment, the brake can be activated if none of the at least one sensor unit determines contact by the operator. In this case it can be assumed that the operator of the microtome in any case does not actively actuate the actuating element in order to perform the relative motion between the object and the knife blade. Thus, it might be possible that the operator works on the object to be cut or adjusts the same or performs a completely different action. Since the relative motion between the object and the blade knife only has to be performed during cutting of the object and thus, apart from that, the object or the object head can be locked, it is irrelevant which action is actually performed by the operator when he does not contact the actuating element. In such a case, the object is locked anyway and the risk of injury for the operator to cut himself/herself on the knife blade given an unintended movement of the object is considerably reduced. Further, it could be provided that the brake can be deactivated if at least one sensor unit determines contact by the operator. In this case, it can be assumed that the operator contacts the actuating element because he/she wishes to control the movement mechanism so that the relative motion between the object and the knife blade is performed and the object is cut. For this, the brake has to be deactivated.

Preferably, a control unit could be provided, which is—preferably electronically—connected to the at least one sensor unit and the brake. The control unit could have a printed circuit board with electronic components and an electrical circuit. The control unit could be arranged within the microtome housing and/or near the at least one sensor unit.

Specifically, with the aid of a sensor unit a first signal could be generated if an operator contacts the sensor unit. The sensor unit could then or almost without delay feed the first signal to the control unit. The control unit could generate at least one signal for deactivating the brake and feed this signal to the brake. With the aid of this signal, the brake could eventually be deactivated, wherein by means of this signal a corresponding actuator of the brake could be controlled.

A second signal could be generated with the aid of a sensor unit if an operator does not contact the sensor unit. The sensor unit could then and likewise almost without delay feed the second signal to the control unit. For activation of the brake, the control unit could generate at least one signal and feed this signal to the brake. The first or the second signal could each have the value zero so that in other words no signal is generated. Preferably, it is provided that the second signal has the value zero or does not have to be generated. In this case, the sensor unit does not determine any contact by the operator, and the brake is to be activated. According to this preferred embodiment, this is the normal state of the locked movement mechanism. The normal state shall only be changed if an operator contacts the sensor unit and thus wishes to control the movement mechanism for a relative motion between the object and the knife blade with the aid of the actuating element. For this, it is eventually provided that, actively, the first signal is generated.

The sensor unit could have an electrically conductive area. The electrically conductive area is arranged electronically insulated relative to further components of the microtome. The electrically conductive area is connected to an electrical circuit. By means of the electrical circuit, a contact of the electrically conductive area can be determined. The electrically conductive area could have a hot embossing foil of stainless steel, which foil could be arranged on the outer surface of the microtome housing in an area which is adjacent to the actuating element. Advantageously, the hot embossing foil of stainless steel can be directly adapted to the shape of the housing since it can be formed flexibly.

In principle, the sensor unit can have a proximity sensor or a contact sensor or, respectively, touch sensor. In one embodiment, it could be provided that with the aid of the proximity sensor it can be detected that a contact by the operator is to be expected if the approach of the hand of the operator below a predeterminable distance value is determined. Additionally or alternatively, it could be provided that an operator actually has to contact the actuating element so that the brake is controlled in accordance with the control logic. A foil contact sensor could in particular be provided as the touch sensor. A proximity sensor will usually have a capacitive sensor.

Specifically, the actuating element could have a handwheel. The actuating element is connected in a rotatably fixed manner to a shaft or axle indirectly or directly driving the movement mechanism. The shaft is rotatably mounted relative to the microtome housing by means of at least one bearing. Such a design is in particular functional in the case of a rotary microtome. Now, a sensor unit could be arranged on the surface of the actuating element or, respectively, the handwheel. Thus, the sensor unit or, respectively, the part of the sensor unit with which an approach or a contact by the operator can be detected moves together with the actuating element. In other words, the actuating element could have a hot embossing foil of stainless steel. A corresponding electronic circuit could either be arranged inside the actuating element—likewise moving together with the actuating element. Alternatively, such a circuit could be arranged stationarily inside the microtome. So that the sensor unit as well as the actuating element have the same electrical potential, the shaft could be designed electrically conductive and have an electrically non-conductive area. The electrically non-conductive area could now be arranged such that an electric conductivity is given between the sensor unit, the conductive area of the shaft and the bearing. Further, it would be necessary that an electric insulation is given between further components of the microtome and the sensor unit, the conductive area of the shaft and the bearing. The electrically non-conductive area could have a non-conductive plastic area in the longitudinal direction of the shaft, i.e. in axial direction. Alternatively, it could also be provided that the shaft has, for example, a hollow cylindrical-shaped plastic area in radial direction, over which area a conductively designed hollow shaft area extends in parts.

In principle, the microtome could be provided in the form of a rotary microtome, a slide microtome, a vibratome or a disc microtome. In particular, it could be provided that the microtome is designed in the form of a cryostat microtome, where the object, the knife blade and the movement mechanism are arranged in a cooled cryo chamber, and the actuating element can be manually actuated from the outside. A sensor unit would have to be provided on the actuating element which can be accessed from the outside.

In a preferred embodiment it is provided that the actuating element can be manually actuated by an operator and, as a result thereof, a shaft can be rotated. Via the shaft, the movement mechanism for performing the relative motion between the object and the knife blade can be driven. This can be effected directly or indirectly via a toothed belt or a gear. An actuator and a brake unit are provided. The brake unit is connected to the shaft in a rotatably fixed manner. By means of the actuator, the brake unit can be automatically placed into a brake position, in which the shaft can be connected in a rotatably fixed manner to the housing or a component part fixed to the housing. In other words, the brake unit is provided on the shaft and not, for example, on the slide guide of the object head. As a result thereof, a compact construction of the device for controlling a brake and of the brake itself is possible since, on the one hand, the sensor unit is arranged on the actuating element or adjacent thereto, and, on the other hand, the actuator of the brake unit is likewise arranged on the shaft in close proximity to the actuating element.

With regard to a method, the object mentioned at the beginning is solved by the features described herein. Accordingly, a method for controlling a brake of a microtome is defined. The microtome comprises an actuating element, a movement mechanism and a brake. With the movement mechanism, an object to be cut is moved relative to a knife blade. The actuating element is manually actuated by an operator. As a result thereof, the relative motion between the object and the knife blade is performed by the movement mechanism. With the aid of the brake, the relative motion can be locked. At least one sensor unit is provided which is provided on the actuating element or adjacent to the actuating element. With the sensor unit, a contact by the operator is determined. The brake is controlled depending on a contact by the operator that is determined or detected or not determined or not detected by the at least one sensor unit.

The method according to the invention is particularly suitable for operating a device as described herein so that, for avoiding repetitions with regard to the device features on this matter, reference is made to the preceding part of the description. In this connection, the method steps required for operating the device become evident to the person skilled in the present art in knowledge of the disclosure of the preceding part of the description.

There are different possibilities of configuring and developing the teaching of the present invention in an advantageous manner. Reference is to be made, on the one hand, to the claims which are dependent on claim 1 and, on the other hand, to the following explanation of the preferred embodiments of the invention with reference to the drawing. In connection with the explanation of the preferred embodiments of the invention with reference to the drawing, also generally preferred embodiments and developments of the teaching are explained.

FIG. 2 shows in a sectional view a schematic illustration of a part of a microtome with a second embodiment of an inventive device for controlling a brake.

Equal or similar parts are identified by identical reference signs in the Figures.

Figure 1:
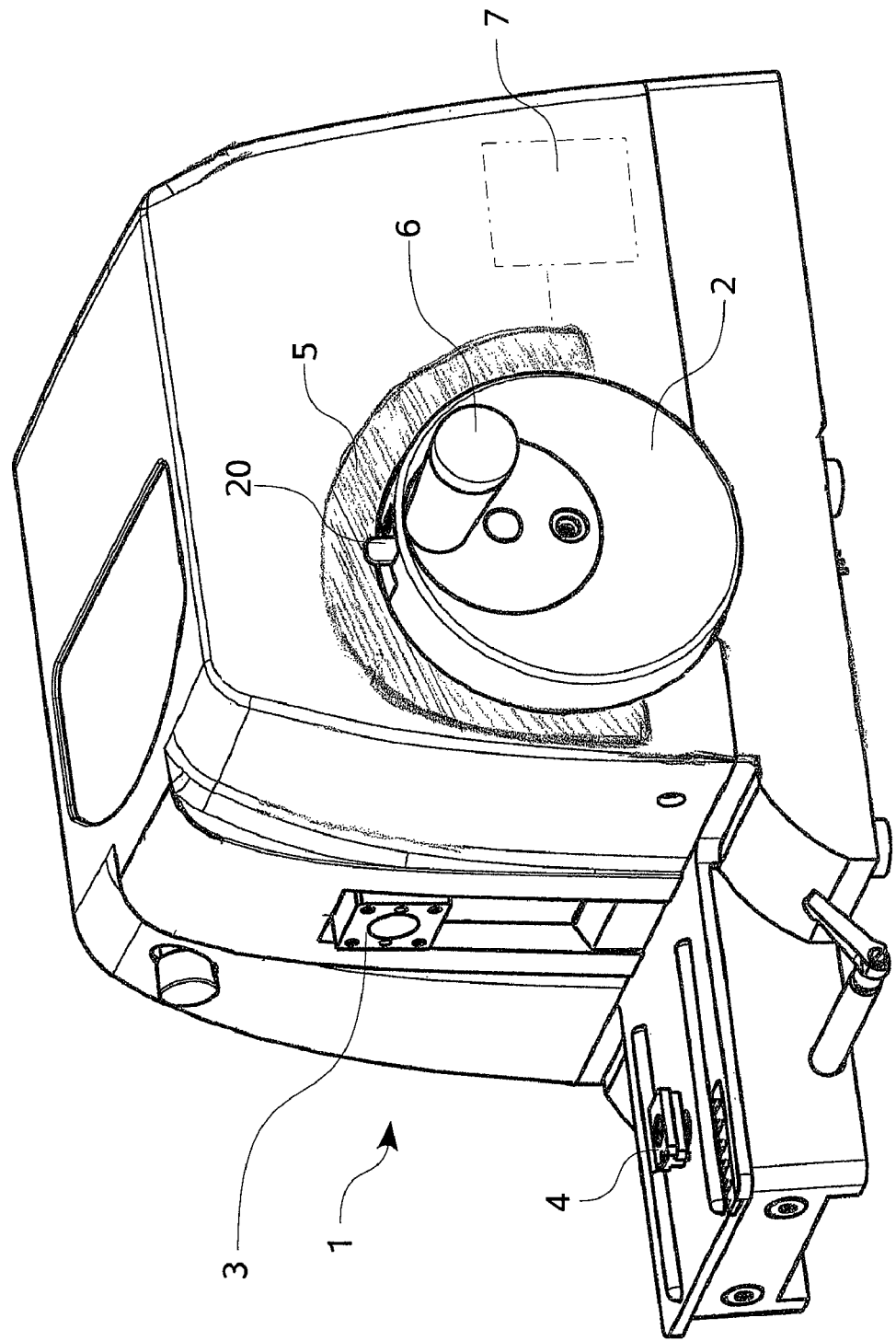
FIG. 1 shows a schematic illustration of a first embodiment of a microtome with an inventive device for controlling a brake.

FIG. 1 shows a microtome 1 which is designed in the form of a rotary microtome. The microtome 1 has an actuating element 2, a movement mechanism not illustrated in FIG. 1 and a non-illustrated brake. The actuating element 2 is designed in the form of a handwheel and can be manually rotated by an operator. As a result thereof, with the movement mechanism provided inside the microtome, the holder 3 for the object head (not illustrated) is moved upwards and downwards in vertical direction. Due to this vertical movement of the holder 3, the (non-illustrated) object head mounted on the holder 3 performs with an object to be cut a relative motion to a knife blade. Neither the knife blade nor the knife holder is shown in FIG. 1. The knife holder can be adapted to the microtome 1 at the mounting place 4 provided therefor.

With the aid of an automatically actuatable brake that is not illustrated in FIG. 1, the relative motion between the object and the knife blade can be locked. The inventive device for controlling the brake of the microtome 1 comprises the sensor unit 5 which is provided adjacent to the actuating element 2. With the aid of the sensor unit 5, a contact of the actuating element 2 by the operator can be determined, when the operator, when grasping the handle 6, also contacts the sensor unit 5. When the sensor unit 5 detects or determines that it is contacted by the operator, the brake is controlled accordingly. In case the brake was activated, the brake is released.

If the sensor unit 5 does not determine a contact by the operator, the brake is activated so that a relative motion between the object and the knife blade is not possible.

Merely shown in broken lines it is indicated that a control unit 7 is provided which is electronically connected to the sensor unit 5 and the brake. With the aid of a sensor unit 5, a first signal is generated if an operator contacts the sensor unit 5. The sensor unit 5 feeds the first signal to the control unit 7. Hereupon, the control unit 7 generates at least one signal for deactivation of the brake and feeds this signal to the brake.

If an operator does not contact the sensor unit 5, the sensor unit 5 does not generate a signal. The control unit 7 is programmed such that in such a case a corresponding signal is automatically generated for activation of the brake and is fed to the brake.

The sensor unit 5 has an electrically conductive area which is designed in the form of a hot embossing foil of stainless steel. The hot embossing foil of stainless steel is arranged electronically insulated with respect to further components of the microtome 1. The hot embossing foil of stainless steel is connected to an electrical circuit of the control unit 7. With the aid of the electrical circuit of the control unit 7, a contact of the electrically conductive area can be determined and the automatic brake can be controlled accordingly. The sensor unit 5 is designed in the form of a contact sensor.

FIG. 2 shows in a sectional view a part of a microtome 1 according to a second embodiment. The microtome 1 according to FIG. 2 is likewise a rotary microtome which has an actuating element 2 designed in the form of a handwheel. The actuating element 2 is connected in a rotatably fixed manner to a shaft 9 driving the movement mechanism 8. The shaft is rotatably mounted relative to the microtome housing 12 with the aid of two bearings 10, 11.

Both the surface of the actuating element 2 and the surface of the handle 6 have a sensor unit 13. The sensor unit 13 has a foil contact sensor. The shaft 9 is formed in several pieces and has a first area 19, a second area 14 and a third area 15. The first area 19 and the third area 15 are formed electrically conductive. The second area 14 is formed electrically non-conductive. The first area 19 of the shaft 9 is in electrical contact with the sensor unit 13 and the bearing 10. The bearing 10 is electrically insulated relative to the microtome housing 12 by the insulating layer 16 and from the rest of the components of the microtome 1. However, the bearing 10 is electrically connected to the control unit 7 via the connection line 17. Thus, the sensor unit 13, the first area 19 of the shaft 9 and the bearing 10 have the same electric potential which can be detected by the control unit 7. When an operator contacts the actuating element 2 or the handle 6, this can be detected by the control unit 7 and the brake 21 can be controlled accordingly depending thereon. Between the first area 19 and the third area 15 of the shaft 9, the second, electrically non-conductive area 14 is arranged. With the second area 14 of the shaft 9, thus also the sensor unit 13, the actuating element 2, the handle 6, the first area 19 of the shaft 9 and the bearing 10 can be electrically insulated from the remaining components of the microtome 1.

On the microtome housing 12, a sensor unit 5 is provided which is designed in the form of a hot embossing foil of stainless steel, which sensor unit 5 is electrically connected to the control unit 7 by means of the connection line 18. Thus, the microtome 1 from FIG. 2 has two sensor units 5 and 13. When an operator contacts one of the sensor units 5, 13 or both sensor units 5, 13, the brake 21 which brakes the object head is automatically released.

In FIG. 1, a locking lever 20 that can be mechanically actuated by an operator and is provided on the actuating element 2 or the handwheel is shown. With the locking lever 20, the handwheel and thus the movement mechanism and eventually also the object head can be mechanically locked in that a part of the locking lever 20 (not shown) engages a recess (not shown) on the microtome 1 in a form-fitting manner and thus locks the handwheel with respect to the microtome housing. Since this requires an additional hand movement or work step, the locking lever 20 can be dispensed with since the microtome 1 according to FIG. 1 has an inventive device for controlling a brake.

Finally, it is particularly pointed out that the above explained embodiments merely serve to describe the claimed teaching but do not restrict the teaching to the embodiments.

LIST OF REFERENCE SIGNS 1 microtome
2 actuating element
3 holder for an object head
4 mounting place of a knife holder
5 sensor unit
6 handle of (2)
7 control unit
8 movement mechanism
9 shaft with which (8) can be driven
10 first bearing for (9)
11 second bearing for (9)

12 microtome housing
13 sensor unit
14 second area of (9)
15 third area of (9)
16 insulating layer
17 electrical connection between (10) and (7)
18 electrical connection between (5) and (7)
19 first area of (9)
20 locking lever
21 brake

The invention claimed is:

1. A brake controlling device and microtome, the microtome (1) having a housing, an actuating element (2), a movement mechanism (8) and a brake capable of rotationally fixing the movement mechanism to the housing or a component fixed on the housing, wherein the movement mechanism (8) moves an object to be cut relative to a knife blade, wherein the actuating element (2) can be manually actuated by an operator and as a result thereof, with the aid of the movement mechanism (8) the relative motion between the object and the knife blade can be performed, and wherein with the aid of the brake the relative motion can be locked relative to the housing and the object, characterized by at least one sensor unit (5, 13) which is provided on the actuating element (2) or the housing and with which contact by the operator can be determined, the brake being controlled according to the determined contact by the at least one sensor unit (5, 13);
wherein the movement mechanism is not driven by an electric motor.

2. The device according to claim 1, characterized in that the brake can be activated if none of the at least one sensor unit (5, 13) determines a contact by the operator or in that the brake can be deactivated if at least one sensor unit (5, 13) determines a contact by the operator.

3. The device according to claim 1, characterized in that a control unit (7) is provided, which is electronically connected to the at least one sensor unit (5, 13) and the brake.

4. The device according to claim 3, characterized in that with the aid of a sensor unit (5, 13) a first signal can be generated if an operator contacts the sensor unit (5, 13), in that the sensor unit (5, 13) feeds the first signal to the control unit (7), and in that the control unit (7) generates at least one signal for deactivation of the brake and feeds this signal to the brake.

5. The device according to claim 3, characterized in that with the aid of a sensor unit (5, 13) a second signal can be generated if an operator does not contact the sensor unit (5, 13), in that the sensor unit (5, 13) feeds the second signal to the control unit (7) and in that for activation of the brake the control unit (7) generates at least one signal and feeds this signal to the brake.

6. The device according to claim 1, characterized in that the sensor unit (5, 13) has an electrically conductive area which is arranged electronically insulated with respect to further components of the microtome (1) and which is connected to an electrical circuit, and in that with the electrical circuit a contact of the electrically conductive area can be determined.

7. The device according to claim 6, characterized in that the electrically conductive area is a hot embossing foil of stainless steel.

8. The device according to claim 1, characterized in that the sensor unit (5, 13) has one or more of the following: a proximity sensor or a contact sensor.

9. The device according to claim 8, characterized in that the proximity sensor or the contact sensor is a foil contact sensor.

10. The device according to claim 8, characterized in that the proximity sensor or the contact sensor is a capacitive sensor.

11. The device according to claim 1, characterized in that the actuating element (2) has a handwheel, in that the actuating element (2) is connected in a rotatably fixed manner to a shaft (9) driving the movement mechanism (8), and in that the shaft (9) is rotatably mounted relative to the microtome housing (12) by at least one bearing (10, 11).

12. The device according to claim 11, characterized in that a sensor unit (13) is arranged on the surface of the actuating element (2), in that the shaft (9) is designed electrically conductive and has an electrically non-conductive area (14) which is arranged such that an electrical conductivity between the sensor unit (13), the conductive area (19) of the shaft (9) and the bearing (10) is given and in that an electrical insulation between further components of the microtome (1) and the sensor unit (13), the conductive area (19) of the shaft (9) and the bearing (10) is given.

13. The device according to claim 1, characterized in that the microtome (1) is designed in the form of a rotary microtome, a slide microtome, a vibratome or a disc microtome.

14. The device according to claim 1, characterized in that the actuating element (2) can be manually operated by an operator and, as a result thereof, a shaft (9) can be rotated, and wherein via the shaft (9) the movement mechanism (8) for performing the relative motion between the object and the knife blade can be driven, in that an actuator and a brake unit are provided, in that the brake unit is connected in a rotatably fixed manner to the shaft (9), in that with the aid of the actuator the brake unit can be automatically placed into the brake position in which the shaft (9) can be connected in a rotatably fixed manner to the housing (12).

15. A method for controlling a brake of a microtome, in particular for operating a device according to one of the claims 1 to 14, wherein the microtome (1) has an actuating element (2), a movement mechanism (8) and a brake, wherein with the aid of the movement mechanism (8) an object to be cut is moved relative to a knife blade, wherein the actuating element (2) is manually actuated by an operator and, as a result thereof, with the movement mechanism (8) the relative motion between the object and the knife blade can be performed, and wherein with the aid of the brake the relative motion can be locked,
characterized by at least one sensor unit (5, 13) which is provided on the actuating element (2) or adjacent to the actuating element (2) and with which a contact by the operator can be determined, the brake being controlled according to the determined contact by the at least one sensor unit (5, 13).

* * * * *